(12) United States Patent
Gazit et al.

(10) Patent No.: US 11,413,477 B2
(45) Date of Patent: Aug. 16, 2022

(54) TRANSFECTION AND DRUG DELIVERY

(71) Applicants: CEDARS-SINAI MEDICAL CENTER, Los Angeles, CA (US); THE REGENTS OF THE UNIVERSITY OF CALIFORNIA, Oakland, CA (US)

(72) Inventors: Dan Gazit, Los Angeles, CA (US); Gadi Pelled, Los Angeles, CA (US); Katherine W. Ferrara, Davis, CA (US); Douglas N. Stephens, Davis, CA (US)

(73) Assignees: CEDARS-SINAI MEDICAL CENTER, Los Angeles, CA (US); THE REGENTS OF THE UNIVERSITY OF CALIFORNIA, Los Angeles, CA (US)

( * ) Notice: Subject to any disclaimer, the term of this patent is extended or adjusted under 35 U.S.C. 154(b) by 446 days.

(21) Appl. No.: 16/348,320

(22) PCT Filed: Nov. 20, 2017

(86) PCT No.: PCT/US2017/062640
§ 371 (c)(1),
(2) Date: May 8, 2019

(87) PCT Pub. No.: WO2018/098091
PCT Pub. Date: May 31, 2018

(65) Prior Publication Data
US 2020/0078607 A1 Mar. 12, 2020

Related U.S. Application Data

(60) Provisional application No. 62/425,546, filed on Nov. 22, 2016.

(51) Int. Cl.
*A61N 7/00* (2006.01)
*G01S 15/89* (2006.01)
(Continued)

(52) U.S. Cl.
CPC .............. *A61N 7/00* (2013.01); *A61B 8/0875* (2013.01); *A61B 8/4218* (2013.01);
(Continued)

(58) Field of Classification Search
CPC .............. A61N 7/00; A61N 2007/0095; A61N 2007/0091; A61N 2007/0013;
(Continued)

(56) References Cited

U.S. PATENT DOCUMENTS 6,591,129 B1 7/2003 Ben-Haim et al.
7,686,763 B2 3/2010 Vaf7y et al.
(Continued)

FOREIGN PATENT DOCUMENTS

CA 2981219 A1 10/2016
CN 203059751 U * 7/2013
(Continued)

OTHER PUBLICATIONS

ISR and Written Opinion for PCT/US2017/062640 dated Jan. 29, 2018, 10 pages.
(Continued)

*Primary Examiner* — Boniface Ngathi N
(74) *Attorney, Agent, or Firm* — Day Pitney LLP; Valeriya Svystun

(57) ABSTRACT

An ultrasound transmitter device for treating a patient is provided. The ultrasound transmitter device includes an imaging probe; an imaging array; and a therapeutic ultrasound device, wherein the imaging probe is configured to guide the therapeutic ultrasound device to the patients treatment site by use of ultrasound imaging with the imaging
(Continued)

array, wherein the therapeutic ultrasound device is configured to produce a controlled intensity of ultrasound energy for treating the patients treatment site, and wherein the imaging probe and the therapeutic ultrasound device are configured to work in conjunction with one another to apply therapeutic ultrasound to tissue or bone graft sites in the patient.

20 Claims, 10 Drawing Sheets

(51) Int. Cl.
*A61B 8/00* (2006.01)
*A61N 7/02* (2006.01)
*A61M 37/00* (2006.01)
*A61B 8/08* (2006.01)

(52) U.S. Cl.
CPC .. *A61M 37/0092* (2013.01); *A61N 2007/0013* (2013.01); *A61N 2007/0091* (2013.01); *A61N 2007/0095* (2013.01); *A61N 2007/027* (2013.01); *G01S 15/899* (2013.01)

(58) Field of Classification Search
CPC ............ A61N 2007/027; A61B 8/4218; A61B 8/0875; A61B 8/085; A61B 8/4209; A61B 2017/2208; A61B 2090/378; A61M 37/0092; G01S 15/899
See application file for complete search history.

(56) References Cited

U.S. PATENT DOCUMENTS

| 8,702,662 | B2 | 4/2014 | Boyle |
| 2003/0078227 | A1 | 4/2003 | Greenleaf et al. |
| 2008/0200806 | A1* | 8/2008 | Liu .......................... A61N 7/02 600/439 |
| 2014/0142468 | A1* | 5/2014 | Hossack ............ A61B 17/2202 601/2 |
| 2015/0165243 | A1 | 6/2015 | Slayton et al. |
| 2018/0169444 | A1* | 6/2018 | Averkiou ............... A61B 8/085 |
| 2020/0078607 | A1 | 3/2020 | Gazit et al. |

FOREIGN PATENT DOCUMENTS

| EP | 3100767 A1 * | 12/2016 | .......... A61B 8/4488 |
| EP | 3544497 | 10/2019 | |
| HK | 40008492 A | 6/2020 | |
| JP | 2020-510452 A | 4/2020 | |
| WO | WO-0243805 A1 * | 6/2002 | ............... A61N 7/02 |
| WO | 2002976508 A1 | 10/2002 | |
| WO | 2006030534 A1 | 3/2006 | |
| WO | WO-2012042494 A1 * | 4/2012 | ............... A61N 7/00 |
| WO | 2016139832 A1 | 9/2016 | |
| WO | WO-2017153799 A1 * | 9/2017 | .......... A61B 8/4477 |
| WO | 2018098091 A1 | 5/2018 | |
| WO | WO-2020237382 A1 * | 12/2020 | .......... A61B 8/5207 |

OTHER PUBLICATIONS

IPRP for PCT/US2017/062640 dated May 28, 2019, 9 pages.
Extended ESR for 17875012.1 dated Jul. 2, 2020, 7 pages.
JP Notice of Reasons for Rejection for JP 2019-527319 dated Aug. 23, 2021, 13 pages.

* cited by examiner

TRANSFECTION AND DRUG DELIVERY

CROSS-REFERENCE TO RELATED APPLICATIONS

This application is the national phase of International Application No. PCT/US2017/062640, filed Nov. 20, 2017, which designated the U.S. and that International Application was published under PCT Article 21(2) in English. This application claims priority under 35 U.S.C. § 119(e) to U.S. Provisional Application No. 62/425,546, filed Nov. 22, 2016, the contents of which are herein incorporated by reference in their entirety.

FIELD OF THE DISCLOSURE

The present invention is directed to a device, a method, and a system for effective tissue healing. More particularly, the disclosed device, method, and system provide a novel tissue healing through use of ultrasound (US) to guide and promote allogeneic transfection and/or drug delivery.

BACKGROUND OF THE DISCLOSURE

The following description includes information that may be useful in understanding the present invention. It is not an admission that any of the information provided herein is prior art or relevant to the presently claimed invention, or that any publication specifically or implicitly referenced is prior art.

Injuries to the skeleton such as nonunion fractures and ligament/tendon tears might have grave consequences for the quality of life of orthopedic patients. Current treatments to nonunion fractures include autografts, which all involve serious complications or side effects. Tears of the anterior cruciate ligament (ACL) or the rotator cuff tendon are often reconstructed using either an autograft or allograft leading to prolonged periods of healing and loss of mobility.

Therefore, a method aiming at reducing the patient recovery time from bone injury and ligament/tendon tears is of great clinical importance.

SUMMARY OF THE DISCLOSURE

Currently, when bone and ligament repairs are widely performed, faster patient healing following a repair procedure would greatly reduce hospital and overall healthcare costs, and improve the patient experience.

There is an unmet need in the field of orthopedic medicine for novel therapies that will enable accelerated bone and ligament/tendon repair. The presently disclosed device and method provide an innovative means to implement more effective tissue healing through the use of ultrasound (US) to guide and promote allogeneic transfection and/or drug delivery.

Research experience recently has shown a technique that can be used to induce bone regeneration through the use of an allogeneic gene, which was transfected in a pig model. Low-intensity pulsed ultrasound (LIPUS) has been known for years to be effective in medicine for both diagnostic and for bone healing, but has also been shown to positively affect autogenous bone graft healing.

Additionally, Bone Morphogenetic Protein (BMP) gene delivery, accomplished using viruses, has been shown to induce healing of nonunion fractures in rodents and large animals and also to enhance ligament integration in several animal models. While viral vectors are the most efficient gene delivery tools, they also introduce potential risks of tumorigenic and immunogenic reactions. Nonviral vectors are considered safer for human use, albeit much less efficient for gene expression. It has been shown that in vivo electroporation used to deliver a BMP gene to endogenous mesenchymal stem cells (MSCs) within a nonunion fracture site in rodents, yielded efficient fracture healing. Yet, an alternative physical method of gene transfection termed sonoporation, or the use of ultrasound for gene delivery, is especially attractive for possible clinical applications due to the widespread use of ultrasound in the clinic today.

However, while ultrasound has been successfully used for BMP gene delivery and ectopic bone formation in rodents, it was much less efficient than electroporation-mediated ectopic bone formation and did not lead to significant bone repair in a nonunion fracture model. Sonoporation and related protocols have now reached human trials for blood-brain-barrier transport enhancement and treatment of acute myocardial infarction; however, sonoporation has failed to reach the level of pre-clinical large animal models and human use in regenerative medicine. In fact, it has been shown that sonoporation can be used to overexpress a reporter gene in a large animal fracture model. Recently, ultrasound-based BMP-6 gene delivery to endogenous MSCs yielded complete segmental bone defect repair in a minipig model. Furthermore, a similar approach was used to deliver plasmid BMP-2 to bone tunnels created for the ACL reconstruction in minipigs' knee joints.

Therefore, disclosed are a device, a method, and a system aimed at speeding up the recovery time of using a practical, minimally invasive approach by conveniently combining at least one ultrasound probe and a system of transfection of genetic materials and/or drug delivery into the patient for the purpose of wound healing. It also aims at a convenient, safe and reliable method to provide genetic material and/or drugs directly to the patient's target site.

The disclosed system and method provide a simple, safe, effective and widely applicable method-device for tissue healing through use of US to guide and promote allogeneic transfection and/or drug delivery.

Additionally, the disclosed system and method may provide accurate allogeneic transfection through use of ultrasound. For instance, disclosed is a combination of at least two ultrasound probes coordinate their use in the procedure to guide and promote the transfection of genetic material into the patient for the purpose of wound healing.

The method of transfection may include, e.g., electroporation, cell squeezing, nanoparticles, magnetofection, microinjection, gene gun, impalefection, hydrostatic pressure, continuous infusion, and sonication and chemical, such as lipofection, and the like.

The method of drug delivery may include focused ultrasound, transient cavitation, and the like.

The disclosed device functions as both an imaging array as well as a therapeutic device, whereby the imaging array is used to guide the position of the therapeutic device. In some embodiments, the combination will also provide the ability to accurate identify treatment site and treat it simultaneously.

In one aspect of the present disclosure, a disclosed ultrasound transmitter device includes at least two ultrasound probes, wherein a first ultrasound probe is configured to be an imaging array, and wherein a second ultrasound probe is configured to be a therapeutic array that is guided to a treatment location in a patient by the first ultrasound probe.

The first ultrasound probe and the second ultrasound probe may be configured to be two removable components that are joined together via a fastening mechanism such as, for example, a clip, a fastener, a nail, a lock, and the like. Alternatively, the two ultrasound probes may be joined together via an adhesive. In yet another embodiment, the two ultrasound probes may be configured to be a single component that is irremovably attached to one another.

In some embodiments, the disclosed treatment device may include gimbal positioner, claim shell, and/or therapeutic array cable. Alternatively, the therapeutic array may be cordless and include its own battery/power source.

Upon guidance to the treatment location, the second ultrasound probe may apply ultrasound treatment to the treatment location. The disclosed treatment device may include a transfection device that is configured to carry out allogeneic transfection on the treatment location. The disclosed treatment device may further include a separate drug delivery device that is configured to carry out effective drug delivery on the treatment location.

In some embodiments, the imaging array may be configured to guide and confirm the position of the therapeutic array. The therapeutic array may include a therapeutic ultrasound treatment device that emits therapeutic beam (e.g., ultrasound) on the patient's treatment site. The therapeutic beam may also guide a drug to the treatment site once the drug is injected/absorbed by the patient.

In some embodiments, the imaging array may be configured to guide and confirm the position of the drug delivery device. The drug delivery device may include its own therapeutic array that is configured to emit a therapeutic beam to guide the drug to the treatment site.

The therapeutic beam may distribute along a beam line in azimuthal dimension while also possessing the ability to dynamically re-position this azimuthally extended beam focus in the elevation dimension. This will allow the therapeutic beam to systematically scan a large region of the patient's treatment site, which provides for a relatively uniform insonation of the intended patient treatment region for the purpose of enhancing allogeneic transfection process.

The extended beam can be swept in any number of ways to accomplish the insonation of a large array; these methods include a) slow or fast concentrated focus sweeping in both azimuthal and elevation (e.g. a raster scan), b) slow or fast extended azimuthal focus scanning in elevation, or c) a combination of (a) and (b) to create the most effective insonation. The acoustic intensity of the beam regardless of the focal shape can be maintained at the desirable intensity (typically about 30 mW/cm2).

In an embodiment, the therapeutic array may be configured as a 1D or 2D array.

In yet another embodiment, the therapeutic array may be steered/directed by, e.g., automatically by a machine that detects the patient's treatment site, mechanically by moving the second ultrasound probe, by use of lens, and by the use of multiple elements and electronic phasing.

The disclosed ultrasound transmitter device can be tailed to a patient's needs: for example, the ultrasound transmitter device may be configured to be applied to a larger scale (e.g., whole shoulder, whole knee, and the like), or treat a smaller scale (e.g., bone tunnel).

In another aspect of the present disclosure, the disclosed ultrasound transmitter includes at least two probes; an imaging array and a therapeutic device, wherein the imaging array may be configured to provide a sufficient resolution to clearly image a bone tunnel or similar which has an ostium of approximately 4 mm in diameter.

The ultrasound transmitter may include a highly adjustable arm that is configured to position the imaging array in a static position while ultrasonically observing the site of the bone tunnel. The adjustable arm may hold the imaging array in a preformed "clam shell". The clam shell may rigidly hold the imaging array, but also permit the imaging array removal and precise replacement at any time necessary. The arm, holding the imaging array, is positioned firstly to clearly observe the bone tunnel and is precisely positioned so that the bone tunnel ostium is centered in the array image at only a few millimeters from the face of the array.

The therapeutic device may emit a therapeutic ultrasound signal and may be capable of dynamically steering its beam energy so this ultrasound signal is distributed in a time-averaged manner to the bone tunnel during the procedure. This second device can be either integrated into the imaging array, or used separately. If used separately, the procedure may be carried out as stated: first, the imaging array locates and centers its view on the bone tunnel, second, the imaging array is removed from its clam shell and an imaging array mimic is used to replace the imaging array which is equipped with a central hole to accommodate the therapeutic US device. In this way, the therapeutic ultrasound device is directly positioned at the bone tunnel without need for imaging itself. The therapeutic ultrasound procedure may be conducted with the cylindrically shaped device and the imaging probe can be used at any time to confirm the position of this therapy device to assure its proper location at the bone tunnel.

In an embodiment, the ultrasound transmitter may include an imaging array with a center space to accommodate the therapeutic ultrasound device, or alternatively, the array can be a complete standard array held in a clam shell holder which can be replaced with an array mimic with a central hole to accommodate the therapeutic ultrasound device.

In an embodiment, the therapeutic device may be capable of ultrasound transmission with low frequency (1 to 2 MHz) emission signals to be used in a typical therapeutic US procedure. The US therapy procedure uses a form of mechanical energy that is transmitted through and into living tissue as acoustic pressure waves. The therapeutic procedure generally utilizes a 20-minute treatment per day of 1-MHz waves repeating at 1 kHz, an average intensity of 30 mW/cm2, and a pulse width of 200 microseconds. The therapeutic US director device is made to distribute the ultrasound energy in a uniform manner within the bone tunnel throughout the therapy procedure. To achieve this and to maintain an atraumatic interface with the tissue the device is built as described below, listed in the order of importance.

1. Ultrasound Energy Production

A simple piezoelectric transducer in a frequency range of 1 to 2 MHz can suffice for the therapeutic ultrasound requirement. This can be a simple disk transducer without backing material and without substantial matching layer design since the required bandwidth is low and the output power is very modest. For a 5 mm diameter transducer the expected electrical impedance will be about 200 Ohms and the transmission sensitivity will be on the order of 5 kPa/V. Therefore the device will require a drive voltage of less than 10 V and electrical power less than 250 mW.

2. Atraumatic Transducer Housing and Placement for Best Insonation of the Tissue to be Treated A material known for its ultrasound transparency such as polymethylpentene (TPX, trade name of Mitsui Plastics) can be used as the housing for the transducer. In this way the transducer and any of its motional parts are completely contained. The housing tube can be arranged with a rounded tip, and can be positioned during the therapeutic ultrasound procedure at or near the bone tunnel ostium. If the imaging array has a center gap to accommodate the ultrasound therapy device, a thin metal band can be secured around the array housing tip to better enable tip visibility by the array for positioning at the bond tunnel. The use of an ultrasound transparent TPX shell tip has been developed and will not appreciably impede the 1.5 MHz echo signal.

3. Beam Steering

At such a low frequency and with very close application of the therapeutic ultrasound power with respect to the tissue, the beam will exist primarily as a radiating spherical wave until it is reflected from the inside of the bone tunnel and becomes a more complicated wave. If the tissue material inside the bone tunnel has an ultrasound attenuation characteristic similar to muscle and liver (i.e. 0.5 dB/cm/MHz) this means that only about 1 dB (20% of the power) will be lost at the end of a 15 mm long bone tunnel. This is very modest attenuation.

To assure that the ultrasound radiation pattern (also known as the "beam") produces a uniform time-averaged insonation in the bone tunnel, the beam can be manipulated to accomplish this. The transducer can exist as either a single or multiple element device. The general beam direction can also be influenced by a mechanical rotation of the transducer or a lens.

The wobbling of the transducer can be accomplished by two means: either a mechanical wobbler or a fixed lens which rotates. In the case of the mechanical wobbler the transducer (either annular array or a single element) can be mounted on a shaft made of a pliable elastomer which encloses the transducer wires and permits a tilt angle of 10 to 15 degrees from the center axis. The green tubular shaft rotates with a single offset ball which tilts the transducer as the tubular shaft rotates.

In the use of the lens, e.g., a TPX (example material here with speed of 2200 m/s) lens, can be made which can steer the beam off axis by about 10 to 15 degrees. The lens can be bonded directly to the transducer front face, or alternatively can rotate within the tip while the transducer can remain fixed in position. In the case of the former, the entire transducer and lens assembly would rotate, or rotate in a +180 deg, −180 deg oscillatory pattern.

The device may have no moving parts and therefore no issues with water or gel coupling (within the tube housing of the transducer). The face of the therapeutic ultrasound transducer would be flat but it would be covered with an ultrasound compatible material to create a dome-like tip. The face of the transducer would have only a few elements, not arranged as an annular array, but more in a matrix fashion. With selection of certain elements (not all), or alternatively selecting all but with changes in phases and/or amplitudes, the beam could be changed enough to accomplish the goal of uniform time-averaged insonation throughout the tissue. Due to the element sizes and frequency (1.5 MHz), it may be necessary to sub-dice the elements to prevent undesirable lateral resonances and promote only the thickness mode resonance in each element. Subdicing is not difficult to do.

The proposed device has great potential to reduce recovery time for patients from bone injury or ligament/muscle tear. The proposed device can also be used to any treatment site that has potential interference to ultrasound from bone structures, such as, for example, brain ((interference from the cranial bones), auditory canal, intra orbital, dental pulp, bone marrow, heart and lungs (interference from ribs), spinal cord and intervertebral discs (interference from vertebrae), cartilage, and the like. Also, conveniently, the disclosed device and method can be used in combination with allogeneic transfection or drug delivery.

The implementation of these devices and methods will result in measurable outcome improvements such as reduction in patient's recovery time, increasing patient comfort and autonomy, reduction in caretaker time, reduction in daily suction sets, among others.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
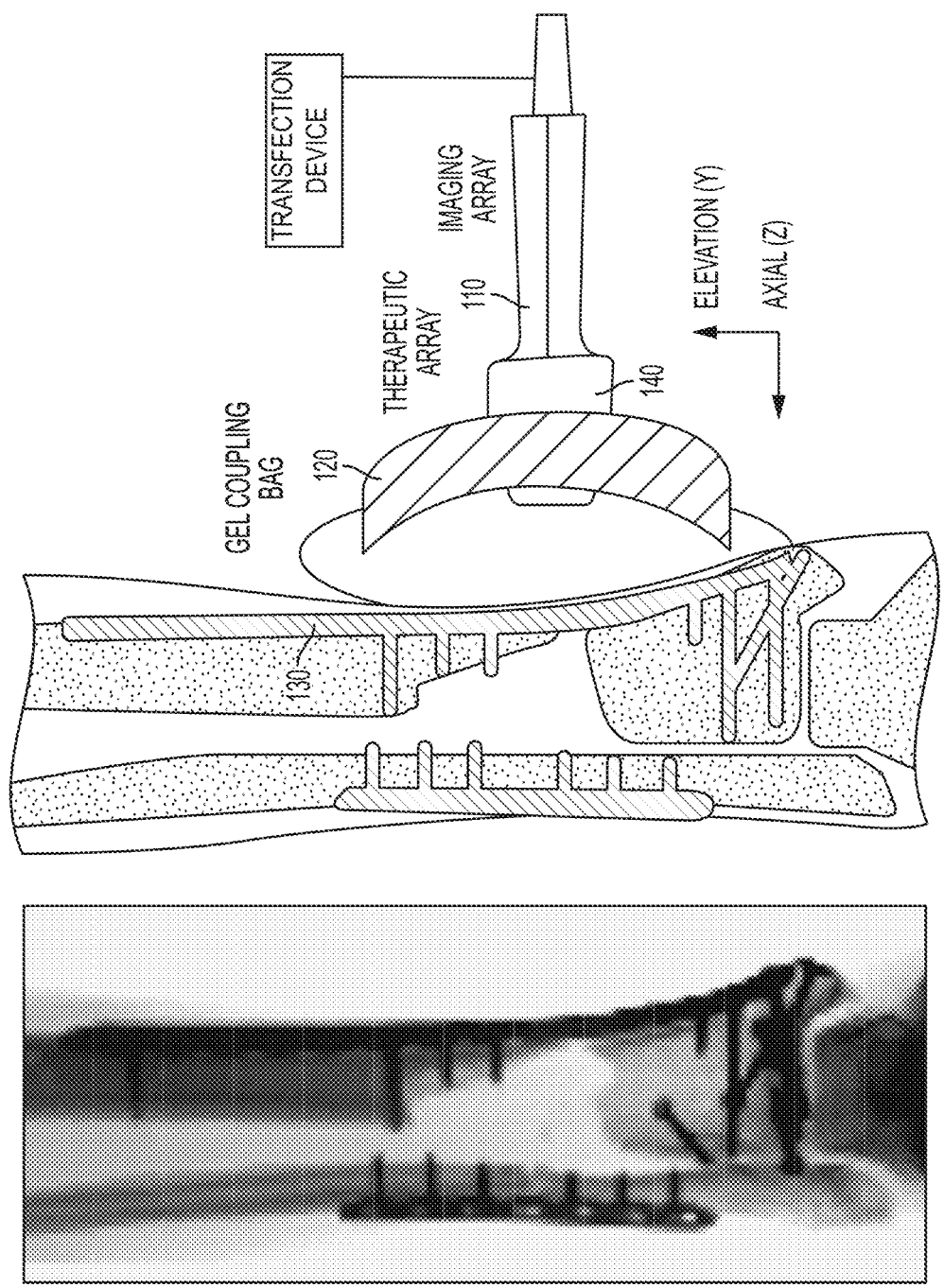
FIG. 1 illustrates an example of a system for healing through ultrasound that is in accordance with the principles of the present disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

The disclosure and the various features and advantageous details thereof are explained more fully with reference to the non-limiting implementations and examples that are described and/or illustrated in the accompanying drawings and detailed in the following description. It should be noted that the features illustrated in the drawings are not necessarily drawn to scale, and features of one implementation may be employed with other implementations as any person skilled in the art would recognize, even if not explicitly stated herein. Descriptions of well-known components and processing techniques may be omitted so as to not unnecessarily obscure the implementations of the disclosure. The examples used herein are intended merely to facilitate an understanding of ways in which the disclosure may be practiced and to further enable those of skill in the art to practice the implementations of the disclosure. Accordingly, the examples and implementations herein should not be construed as limiting the scope of the disclosure.

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

FIG. 1 illustrates an example of an application of a therapeutic device 110 that shows the therapeutic array 120 directed at a complex bone defect repair site 130 involving both the tibia and fibula. The imaging probe 140 guides and confirms the position of the therapeutic array 120. The gimbal positioner, clam shell and therapeutic array cable are omitted in the drawing for brevity. The therapeutic device 110 includes an imaging array that detects the repair site and guides the therapeutic array 120 that applies ultrasound therapy at a predetermined (or dynamically changing based on situation) wavelengths.

The therapeutic device 110 may also include a transfection device or system (not shown) that carries out transfection of genetic materials onto the repair site once such site is identified and located by the imaging probe.

The transfection method/system may include e.g., electroporation, cell squeezing, nanoparticles, magnetofection, microinjection, gene gun, impalefection, hydrostatic pressure, continuous infusion, and sonication and chemical, such as lipofection, and the like.

Figure 2A:
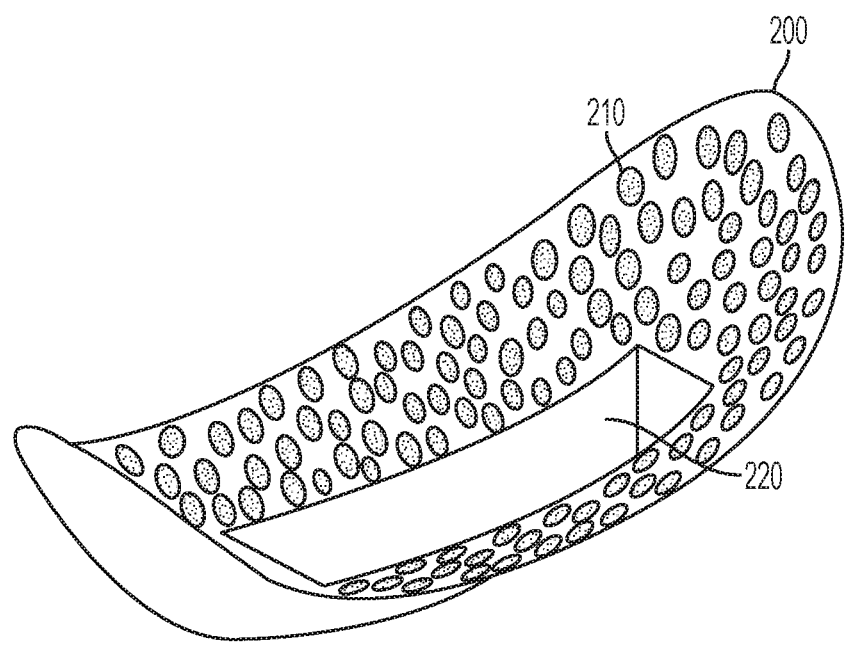
FIGS. 2A-2D illustrate different examples of a steerable therapeutic array in accordance with the principles of the present disclosure.

FIGS. 2A-2D illustrate different examples of a steerable ultrasound beam that is emitted from the therapeutic device that is constructed in accordance with the principles of the present disclosure. FIG. 2A shows an example of a steerable therapeutic array 200 with the long axis shape and general description of the array elements 210 in random (but known) positions covering the array curved surface. As shown, the large therapeutic array may include small elements 210 which are arranged in a random fashion to help avoid undesirable grating lobes when the main focus is steered away from the geometric center focus region 220.

Figure 2B:
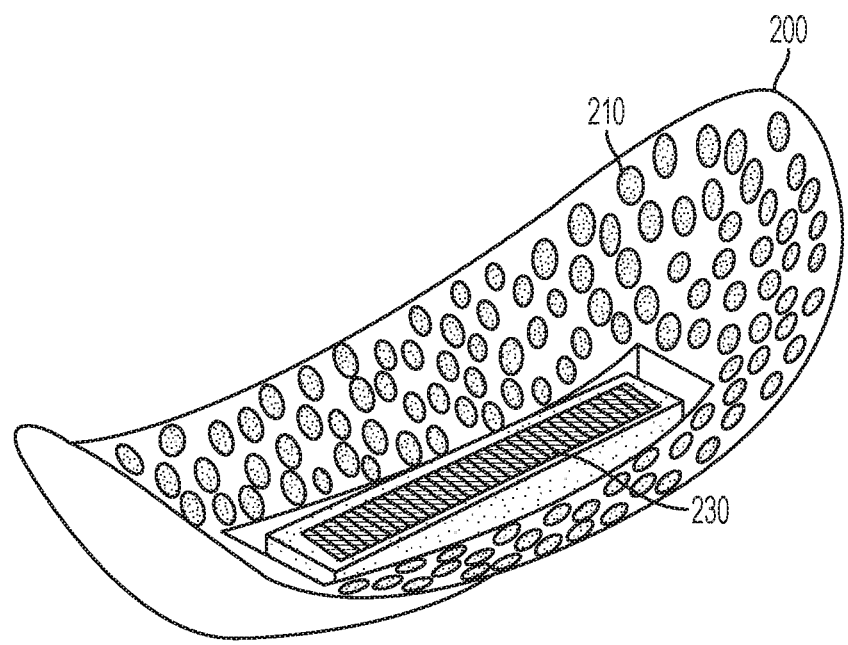

In FIG. 2B, the imaging array 230 has been added showing its alignment along the center axis of the therapeutic array 200. As shown, the key design aspect of this large array 230 is its long azimuthal dimension (rather than being strictly a surface which is a section from a sphere); this is done to enhance the array's ability to create an extended azimuthal focus. In addition a key aspect is the accommodation (a central cavity) for the use of an imaging array.

Figure 2C:
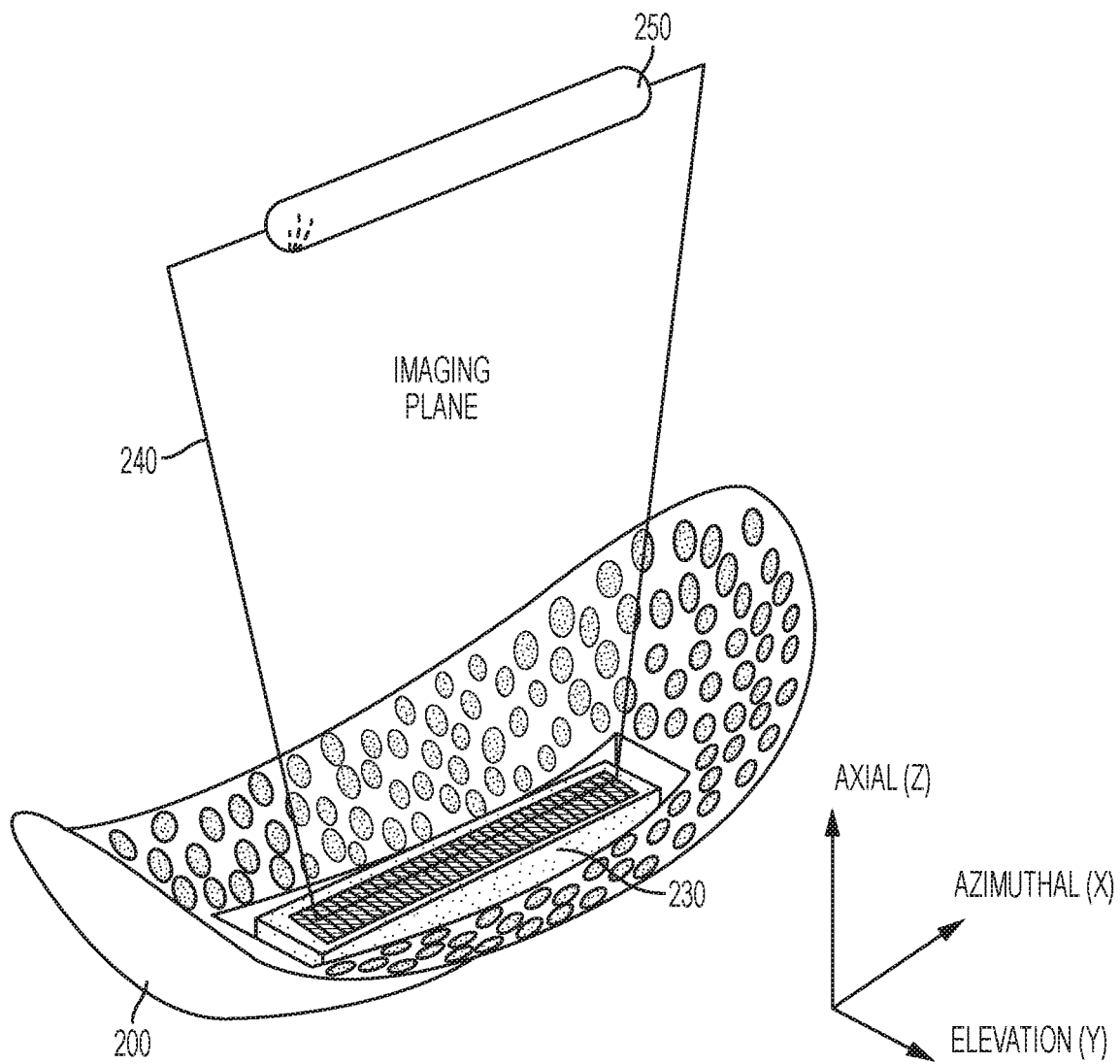

FIG. 2C illustrates an imaging plane 240 and the cylindrical region 250 which is the extended focus region created by the therapeutic array 200. In addition to the use of a relatively standard imaging array for guidance, the key aspect of this device is the ability to create a beam which is distributed along a beam line in the azimuthal dimension while also possessing the ability to dynamically re-position this azimuthally extended beam focus in the elevation dimension. In this manner, a very large region can be systematically scanned which provides for a relatively uniform insonation of the intended region for the purpose of enhancing the allogeneic transfection process. The extended beam can be swept in any number of ways to accomplish the insonation of a large array; these methods include a) slow or fast concentrated focus sweeping in both azimuthal and elevation (e.g. a raster scan), b) slow or fast extended azimuthal focus scanning in elevation, or c) a combination of (a) and (b) to create the most effective insonation. The acoustic intensity of the beam regardless of the focal shape can be maintained at the desirable intensity (typically about 30 mW/cm2).

Figure 2D:
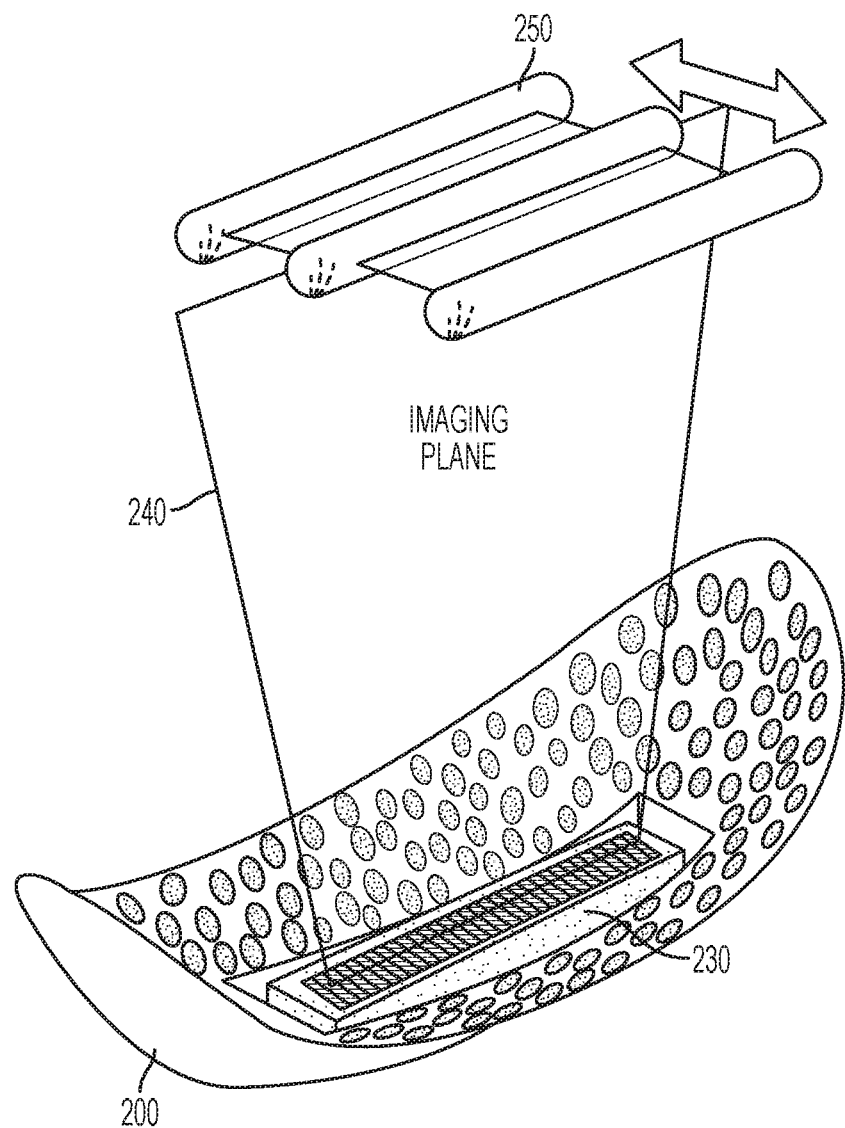

FIG. 2D shows that the extended focus region (as shown in, e.g., FIG. 2C) can be steered in the elevation plane which permits a large net array of therapeutic insonation.

Figure 3A:
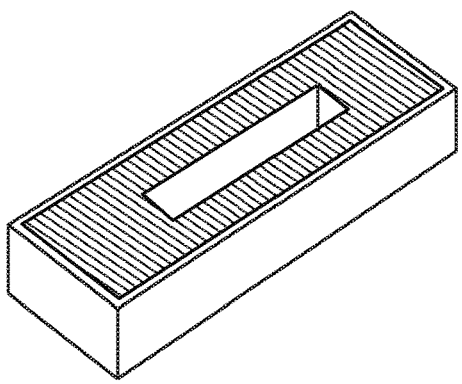
FIGS. 3A-3C illustrate another example of a steerable therapeutic array in accordance with the principles of the present disclosure.
Figure 3B:
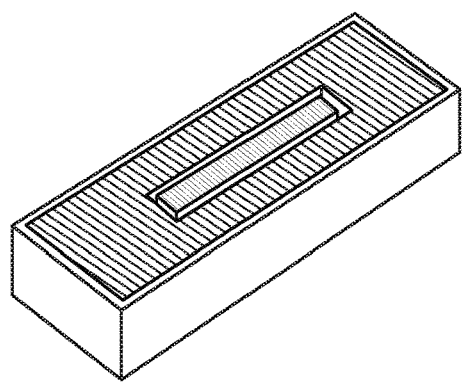
Figure 3C:
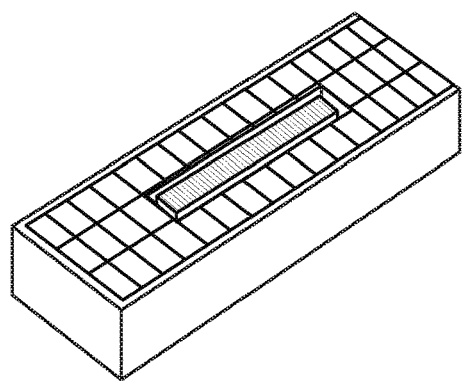

FIGS. 3A-3B illustrate an example of a planar therapeutic array which can be realized as a 1D or 2D array. Since the therapeutic US beam can be very broadly focused while being steered, a large number of elements and a small size in array element are not necessarily required. The steerable therapeutic array is shown as a relatively planar device with elements distributed is such a way to allow a 1D or a 2D array to operate as the low intensity beam transmitter. In FIG. 3A, a planar 1D array is configured with the central slot for the guiding imaging transducer; in FIG. 3B, the array is shown with the imaging transducer array in position; and in FIG. 3C, a 2D segmented array is shown with elements coarse enough to permit both a low channel count but high enough to permit adequate beam steering to insonify the region intended.

Figure 4B:
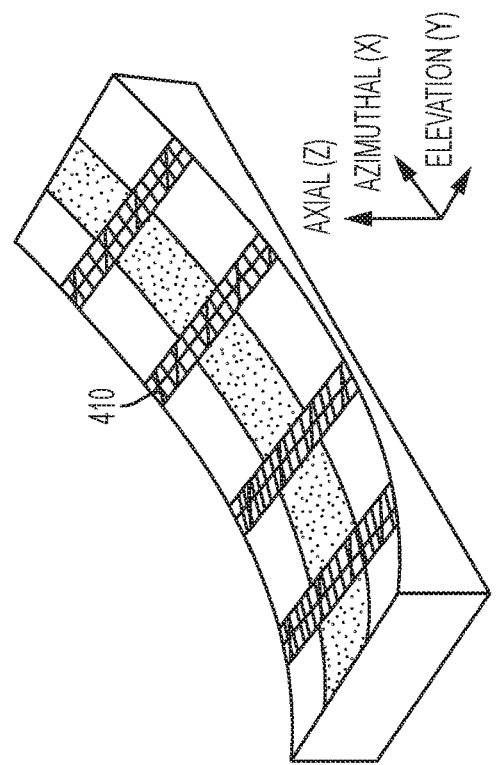
FIGS. 4A and 4B illustrate different views of yet another example of a steerable therapeutic array that in accordance with the principles of the present disclosure.
Figure 4A:
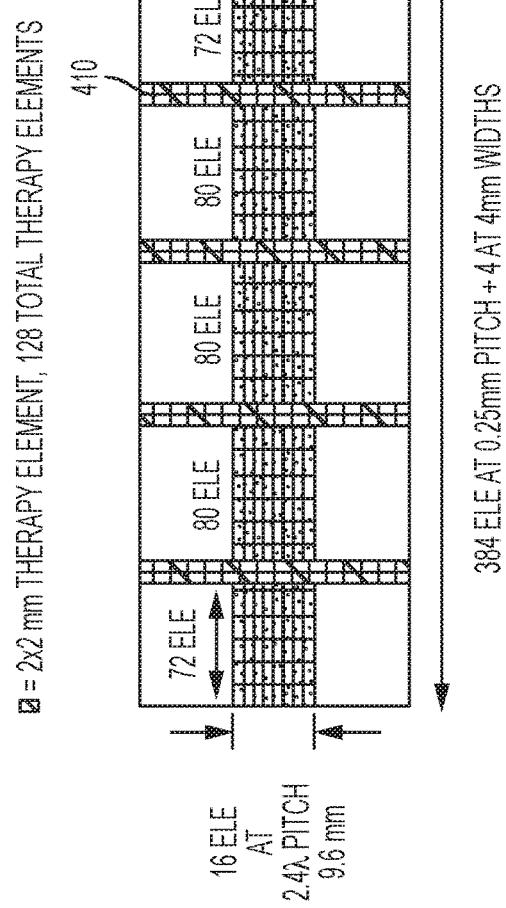

FIGS. 4A and 4B illustrate different views of an example of a steerable therapeutic array that is in accordance with the principles of the present disclosure. The steerable therapeutic array (as shown) with a curved surface and a radius of curvature which is appropriate for the application (e.g., ROC in range of 50 to 75 mm is appropriate for the knee joint application, as depicted in FIG. 1). Since the therapy array does not produce high intensities the therapy array element area 410 is relatively small but permits each element to be phased to allow low frequency steering in virtually any direction. The wide gaps between the 4 groups of therapy sub-arrays will produce "grating lobes" but these will be of little consequence; the exact number and distribution of elements is flexible as this is a generic design example. The imaging elements permit imaging at 6 MHz which will allow for good focusing in both azimuth and elevation at up to 10 cm depths. The imaging plane can be phased in elevation focusing to easily permit a +/−15 degree elevation steering; this can be increased as needed with either lowering the imaging frequency or decreasing the elevation pitch. The imaging here in this design can be accomplished with either standard moving apertures of a linear array, or by summing together sub-apertures in a synthetic aperture realization.

Figure 5B:
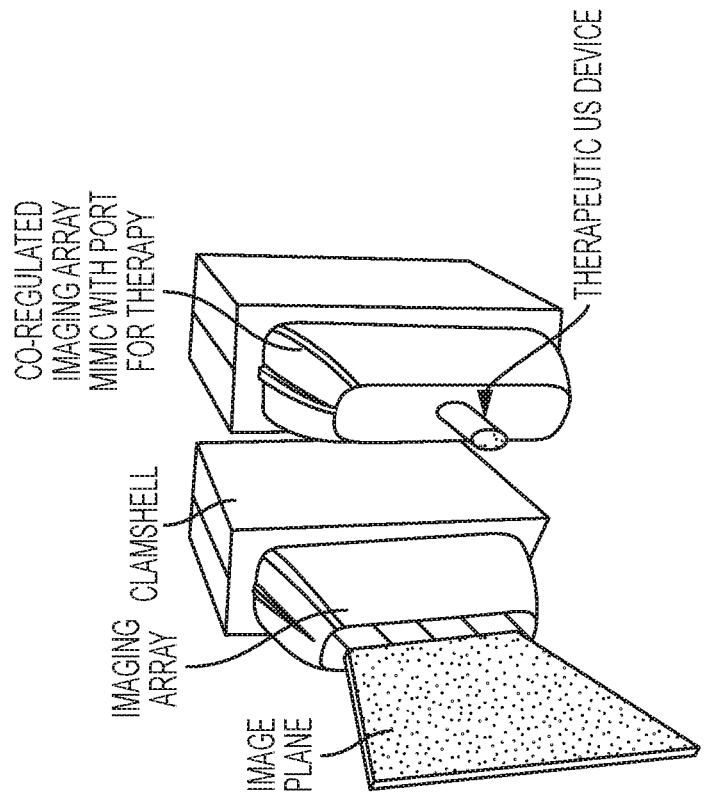
FIG. 5B illustrates yet another example of a therapeutic device that is constructed in accordance with the principles of the present disclosure.
Figure 5A:
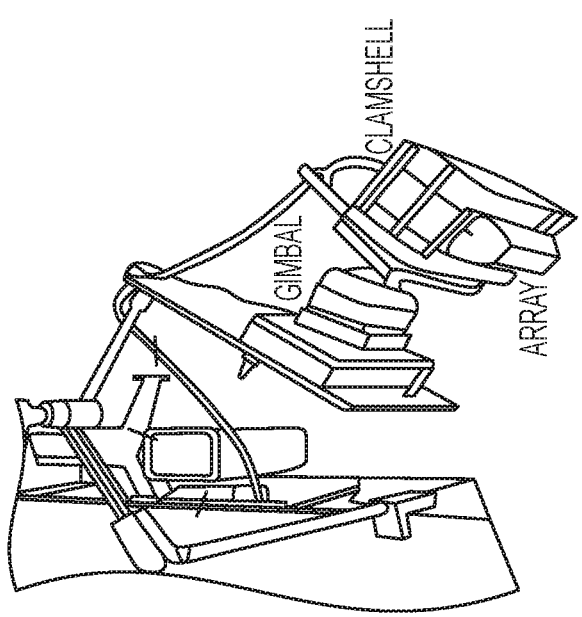
FIG. 5A illustrates an example of a therapeutic device that is constructed in accordance with the principles of the present disclosure.

FIGS. 5A and B illustrate different examples of a therapeutic device that is constructed in accordance with the principles of the present disclosure. This first device may be an ultrasound imaging probe with sufficient resolution to clearly image a bone tunnel or similar which has an ostium of approximately 4 mm in diameter. This device would be supported on a highly adjustable arm (as shown in, e.g., FIG. 5A) which positions the imaging array in a static position while ultrasonically observing the site of the bone tunnel. The adjustable arm may hold the imaging array in a preformed "clam shell" (as shown in, e.g., FIG. 5b). The clam shell rigidly holds the array, but also permits the imaging array removal and precise replacement at any time necessary. The arm, holding the imaging array, may be positioned firstly to clearly observe the bone tunnel and is precisely positioned so that the bone tunnel ostium is centered in the array image at only a few millimeters from the face of the array. The second device emits a therapeutic ultrasound signal and is cable of dynamically steering its beam energy so this ultrasound signal is distributed in a time-averaged manner to the bone tunnel during the procedure. This second device can be either integrated into the imaging array, or used separately. If used separately, the procedure is carried out as stated: Firstly the imaging array locates and centers its view on the bone tunnel, secondly the imaging array is removed from its clam shell and an imaging array mimic is used to replace the imaging array which is equipped with a central hole to accommodate the therapeutic US device (as shown in, e.g., FIG. 5B). In this way, the therapeutic ultrasound device is directly positioned at the bone tunnel without need for imaging itself. The therapeutic ultrasound procedure is conducted with the cylindrically shaped device and the imaging probe can be used at any time to confirm the position of this therapy device to assure its proper location at the bone tunnel.

Figure 6A:
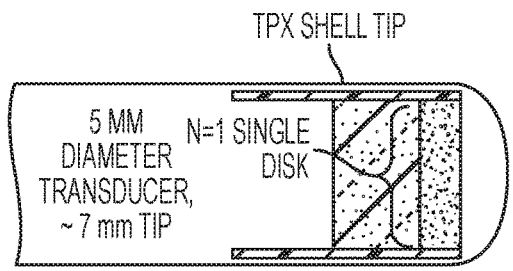
FIGS. 6A-6G illustrate different examples of an ultrasound radiation pattern that is emitted by a therapeutic device that is constructed in accordance with the principles of the present disclosure.
Figure 6E:
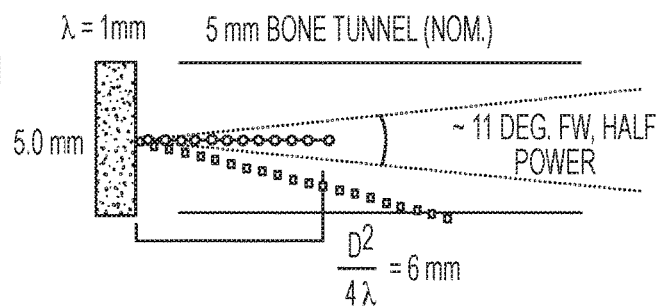
Figure 6B:
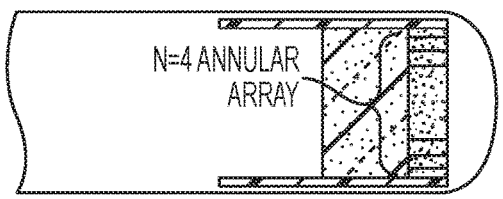
Figure 6C:
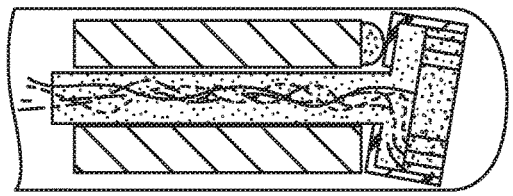
Figure 6F:
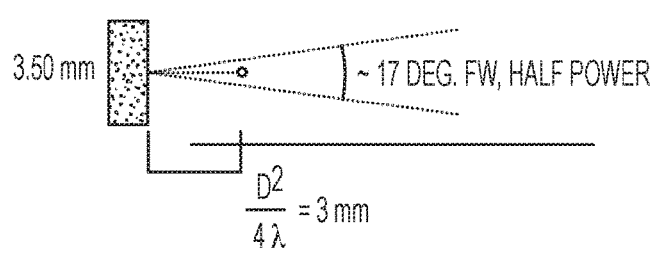
Figure 6D:
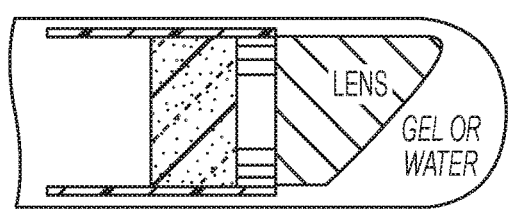
Figure 6G:
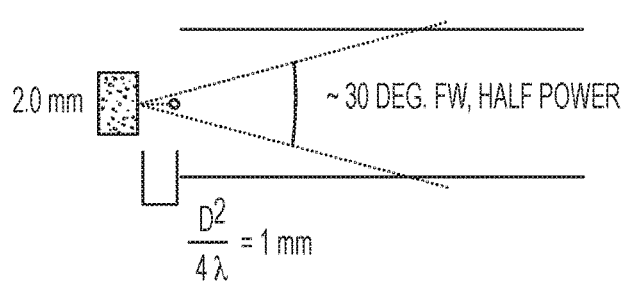

FIGS. 6A-6G illustrate different examples of an ultrasound radiation pattern that is emitted by a therapeutic device that is constructed in accordance with the principles of the present disclosure. Design variants are shown for the therapeutic ultrasound transducer device. In FIGS. 6A-6D, a TPX shell covers the therapy transducer assembly. In FIG. 6A, a single fixed position disk transducer is used; this single element can also be wobbled as in FIG. 6C. In FIG. 6B, an annular array is shown which can produce beams of various widths shown in FIGS. 6E-6G. The beam can be wobbled mechanically as in FIG. 6C, or with a lens as in FIG. 6D.

The wobbling of the transducer can be accomplished by two means: either a mechanical wobbler or a fixed lens which rotates. In the case of the mechanical wobbler (see, e.g., FIG. 2C) the transducer (either annular array or a single element) can be mounted on a shaft (shown in yellow) made of a pliable elastomer which encloses the transducer wires and permits a tilt angle of 10 to 15 degrees from the center axis. The green tubular shaft rotates with a single offset ball which tilts the transducer as the tubular shaft rotates.

In the use of the lens as shown in (d), a TPX (example material here with speed of 2200 m/s) lens can be made which can steer the beam off axis by about 10 to 15 degrees. The lens can be bonded directly to the transducer front face, or alternatively can rotate within the tip while the transducer can remain fixed in position. In the case of the former, the entire transducer and lens assembly would rotate, or rotate in +180 degrees, −180 degrees oscillatory pattern.

Ultimately, the most reliable device would have no moving parts and therefore no issues with water or gel coupling (within the tube housing of the transducer). The face of the therapeutic US transducer would be flat but it would be covered with an ultrasound compatible material to create a dome-like tip. The face of the transducer would have only a few elements, not arranged as an annular array, but more in a matrix fashion. With selection of certain elements (not all), or alternatively selecting all but with changes in phases and/or amplitudes, the beam could be changed enough to accomplish the goal of uniform time-averaged insonation throughout the tissue. Due to the element sizes and frequency (1.5 MHz) it may be necessary to sub-dice the elements to prevent undesirable lateral resonances and promote only the thickness mode resonance in each element. Subdicing is not difficult to do. Examples of the face of the solid state aperture is shown in FIGS. 7A and 7B.

Figure 7A:
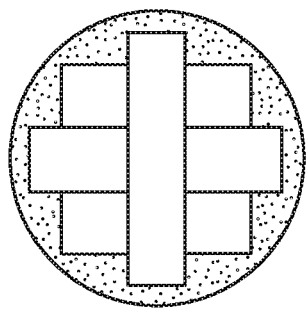
FIGS. 7A and 7B illustrate examples of a solid state array in accordance with the principles of the present disclosure.
Figure 7A:
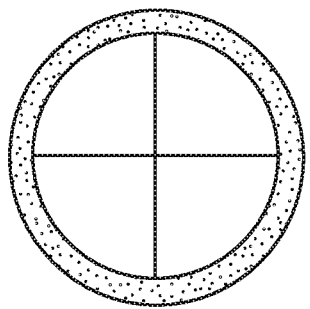
Figure 7A:
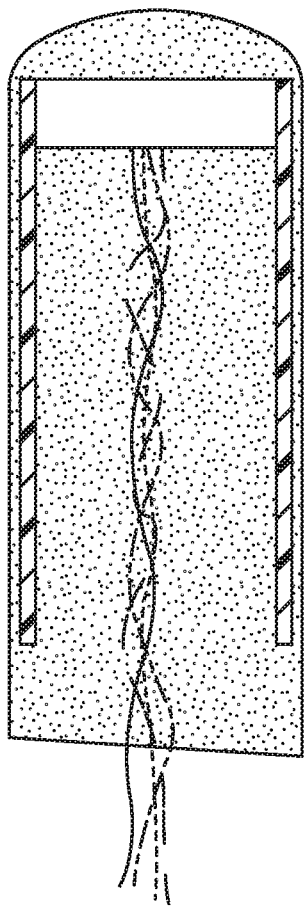
Figure 7B:
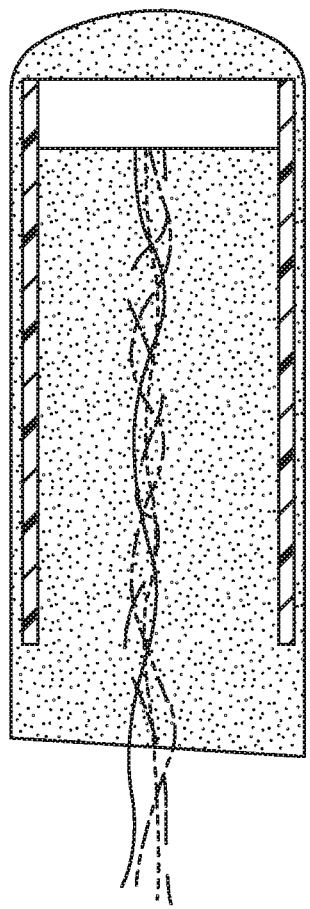

FIGS. 7A and 7B illustrate examples of a solid state array that is in accordance with the principles of the present disclosure. A solid state array is shown with 9 elements in FIG. 7A, which can be phased or weighted as necessary to create a beam which changes in its directivity while maintaining a constant power density for the purposes of therapeutic US. A simple, but likely as effective for signal energy transmission and beam steering, is shown in FIG. 7B with the use of only 4 phased elements.

EMBODIMENTS

Embodiment 1

An ultrasound transmitter device for treating a patient including:
an imaging probe an imaging array; and
a therapeutic ultrasound device,
wherein the imaging probe is configured to guide the therapeutic ultrasound device to the patient's treatment site by use of ultrasound imaging with the imaging array, and
wherein the therapeutic ultrasound device is configured to produce a controlled intensity of ultrasound energy for treating the patient's treatment site.

Embodiment 2

The ultrasound transmitter device of embodiment 1, wherein the imaging probe and the therapeutic ultrasound device are configured to become co-aligned once the imaging probe identifies the patient's treatment site.

Embodiment 3

The ultrasound transmitter device of embodiment 1, wherein the therapeutic ultrasound device includes at least one of: an ultrasound radiator, lens, other elements and phasing needed in applying ultrasound energy.

Embodiment 4

The ultrasound transmitter device of embodiment 3, wherein the ultrasound energy is directed by at least one of the following: mechanically moving an ultrasound radiator, by use of lens, and by use of multiple elements and electronic phasing.

Embodiment 5

The ultrasound transmitter device of embodiment 1 further including a transfection device that is configured to transfect a genetic material onto the patient's treatment site.

Embodiment 6

The ultrasound transmitter device of embodiment 5, wherein the transfection is carried out by at least one of the following: electroporation, cell squeezing, nanoparticles, magnetofection, microinjection, gene gun, impalefection, hydrostatic pressure, continuous infusion, and sonication and chemical.

Embodiment 7

The suction tube of embodiment 1, wherein the suction section is slidably connected to the outside portion the enteric tube to allow the suction tube to slide longitudinally with respect to the enteric tube.

Embodiment 8

The ultrasound transmitter device of embodiment 1 wherein the ultrasound energy is configured to enhance drug delivery on the treatment site by transient cavitation.

Embodiment 9

An ultrasound transmitter device for treating a patient including:
an imaging probe;
an imaging array; and
a therapeutic ultrasound device,
wherein the imaging probe is configured to guide the therapeutic ultrasound device to the patient's treatment site by use of ultrasound imaging with the imaging array,
wherein the therapeutic ultrasound device is configured to produce a controlled intensity of ultrasound energy for treating the patient's treatment site, and
wherein the imaging probe and the therapeutic ultrasound device are configured to work in conjunction with one another to apply therapeutic ultrasound to tissue or bone graft sites in the patient.

Embodiment 10

The ultrasound transmitter device of embodiment 9, wherein the ultrasound transmitter device is configured to operate to form an ultrasound focus to be used to insonate a region of tissue or bone with a controlled means of ultrasound energy production.

Embodiment 11

The ultrasound transmitter device of embodiment 10, wherein the ultrasound focus includes at least one of: a point focus, a distributed focus, or a combination.

Embodiment 12

The ultrasound transmitter device of embodiment 11, wherein the ultrasound transmitter device is configured to move the ultrasound focus to insonate a region of tissues by distributing the ultrasound beam focus energy over a 3 dimensional volume in a swept manner, a simultaneous multi-focused manner, a broad focused manner, or combination of these manners.

Embodiment 13

The ultrasound transmitter device of embodiment 9, wherein the therapeutic ultrasound is configured to enhance drug delivery on the treatment site by transient cavitation.

Embodiment 14

The ultrasound transmitter device of embodiment 9, wherein the ultrasound transmitter device is configured to monitor cavitation of the patient's treatment site.

Embodiment 15

The ultrasound transmitter device of embodiment 14, wherein the ultrasound transmitter device is configured to determine stable cavitation.

Embodiment 16

The ultrasound transmitter device of embodiment 14, wherein the ultrasound transmitter device is further configured to tailor treatment based on determination of stable cavitation.

Embodiment 17

The ultrasound transmitter device of embodiment 14, wherein the ultrasound transmitter device is configured to build a three-dimensional map of the cavitation on the patient's treatment site.

Embodiment 18

The ultrasound transmitter device of embodiment 14, wherein the ultrasound transmitter device is configured to build a one, two, or four-dimensional map of the cavitation on the patient's treatment site.

Embodiment 19

A method for treating a patient including:
providing an ultrasound transmitter device, wherein the device includes:
  an imaging probe
  an imaging array; and
  a therapeutic ultrasound device,
guiding the therapeutic ultrasound device to the patient's treatment site by using the ultrasound imaging emitted from the imaging array that is configured to be placed on or adjacent to the imaging probe; and
producing a controlled intensity of ultrasound energy for treating the patient's treatment site.

Embodiment 20

The method of embodiment 19, wherein the imaging probe and the therapeutic ultrasound device are configured to become co-aligned once the imaging probe identifies the patient's treatment site.

CONCLUSIONS

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:
1. An ultrasound transmitter device for treating a patient comprising:
  an imaging probe comprising an imaging array; and a therapeutic ultrasound device comprising a therapeutic transducer array, the therapeutic transducer array comprising a plurality of transducer elements;
  wherein the therapeutic transducer array has a concave curvature with respect to a patient's treatment site;
  wherein the plurality of therapeutic elements is arranged as a set of therapy sub-arrays;
  wherein any two adjacent therapy sub-arrays of the set of therapy sub-arrays are separated by a gap;
  wherein the gap is a distance between a first longitudinal edge of one therapy sub-array and a second longitudinal edge of another adjacent therapy sub-array, the first longitudinal edge of the one therapy sub-array adjacent to the second longitudinal edge of the another adjacent therapy sub-array;
  wherein the gap between any two adjacent sub-arrays is greater than a respective therapy sub-array width of each therapy sub-array;
  wherein the imaging probe is configured to guide the therapeutic ultrasound device to the patient's treatment site by use of ultrasound imaging with the imaging array; and
  wherein the therapeutic ultrasound device is configured to produce a controlled intensity of ultrasound energy for treating the patient's treatment site.

2. The ultrasound transmitter device of claim 1, wherein respective ultrasound focal regions of the imaging probe and the therapeutic ultrasound device are configured to become co-aligned once the imaging probe identifies the patient's treatment site.

3. The ultrasound transmitter device of claim 1, wherein the therapeutic ultrasound device comprises at least one of: an ultrasound radiator, lens, and electronic phasing needed in applying ultrasound energy; and wherein the ultrasound energy is directed by at least one of the following: mechanically moving an ultrasound radiator, by use of lens, and by use of the plurality of transducer elements and the electronic phasing.

4. The ultrasound transmitter device of claim 1 further comprising a transfection device that is configured to transfect a genetic material onto the patient's treatment site.

5. The ultrasound transmitter device of claim 4, wherein the transfection is carried out by at least one of the following: electroporation, cell squeezing, nanoparticles, magnetofection, microinjection, gene gun, impalefection, hydrostatic pressure, continuous infusion, and sonication and chemical.

6. The ultrasound transmitter device of claim 1, wherein the ultrasound energy is configured to enhance drug delivery or gene delivery on the treatment site by transient cavitation.

7. The ultrasound transmitter device of claim 1, wherein a radius of curvature of the therapeutic transducer array is based on the patient's treatment site.

8. The ultrasound transmitter device of claim 1, wherein the imaging array and the therapeutic transducer array are configured to generate an extended focal region in an azimuthal direction with respect to direction of propagation of ultrasound waves generated by the imaging array and the therapeutic transducer array; and wherein the imaging array and the therapeutic array are configured to steer the extended focal region in an elevation direction with respect to direction of propagation of ultrasound waves generated by the imaging array and the therapeutic transducer array.

9. The ultrasound transmitter device of claim 1, wherein a first total number of transducer elements in the therapeutic transducer array is less than a second total number of imaging transducer elements in the imaging array.

10. The ultrasound transmitter device of claim 1, wherein the therapy sub-arrays of the set of therapy sub-arrays are parallel to each other; wherein the imaging array includes a set of imaging sub-arrays; wherein the set of imaging sub-arrays and the set of therapy sub-arrays are arranged in an alternating manner such that one imaging sub-array alternates with one therapy sub-array; and wherein an imaging sub-array width of any imaging sub-array is greater than the therapy sub-array width of any therapy sub-array.

11. An ultrasound transmitter device for treating a patient comprising:
  an imaging array comprising a set of imaging sub-arrays; and
  a therapeutic transducer array comprising a set of therapy sub-arrays;
    wherein the imaging array and the therapeutic transducer array are concavely curved with respect to a treatment site of the patient;
    wherein any two adjacent therapy sub-arrays of the set of therapy sub-arrays are separated by a gap between a first longitudinal edge of one therapy sub-array and a second longitudinal edge of another adjacent therapy sub-array, the gap having a gap width greater than a respective therapy sub-array width of each therapy sub-array;
    wherein the imaging array is configured to guide the therapeutic transducer array to the treatment site by use of ultrasound imaging with the imaging array;
    wherein the therapeutic transducer array is configured to produce a controlled intensity of ultrasound energy for treating the treatment site; and
    wherein the imaging probe and the therapeutic transducer array are configured to work in conjunction with one another to image the treatment site and apply therapeutic ultrasound to the treatment site.

12. The ultrasound transmitter device of claim 11, wherein the ultrasound transmitter device is configured to operate to form an ultrasound focus to be used to insonate a region of the treatment site with a controlled ultrasound energy production; and wherein the ultrasound focus comprises at least one of: a point focus, a distributed focus, or a combination thereof.

13. The ultrasound transmitter device of claim 12, wherein the ultrasound transmitter device is configured to move the ultrasound focus to insonate the treatment site by distributing the ultrasound beam focus energy over a three-dimensional volume in a swept manner, a simultaneous multi-focused manner, a broad focused manner, or a combination thereof.

14. The ultrasound transmitter device of claim 11, wherein the therapeutic ultrasound is configured to enhance drug delivery on the treatment site by transient cavitation; and wherein the ultrasound transmitter device is configured to monitor cavitation of the treatment site and determine stable cavitation.

15. The ultrasound transmitter device of claim 14, wherein the ultrasound transmitter device is further configured to tailor treatment based on determination of stable cavitation.

16. The ultrasound transmitter device of claim 14, wherein ultrasound transmitter device is configured to build a one, two, three, or four-dimensional map of the cavitation on the treatment site.

17. The ultrasound transmitter device of claim 11, wherein the therapeutic ultrasound array and imaging array are arranged on a same substrate; and wherein an imaging sub-array width of any imaging sub-array is greater than the therapy sub-array width of any therapy sub-array.

18. A method for treating a patient comprising:
providing an ultrasound transmitter device, wherein the ultrasound transmitter device comprises:
an imaging probe comprising an imaging array; and
a therapeutic ultrasound device comprising a therapeutic transducer array, the therapeutic transducer array and the imaging array concavely curved with respect to a treatment site of the patient;
aligning a focal plane of the therapeutic transducer array to the treatment site based on an imaging plane of the imaging array; and
producing a controlled intensity of ultrasound energy for treating the treatment site;
wherein the therapeutic transducer array includes a set of therapy sub-arrays, the set of therapy sub-arrays arranged to provide ultrasound therapy to a target body volume, the target body volume including one or more synthetic implants and/or one or more bone structures;
wherein the any two adjacent therapy sub-arrays of the set of therapy sub-arrays are separated by a gap greater than a respective width of each therapy sub-array; and
wherein the gap is a distance between a first longitudinal edge of one therapy sub-array and a second longitudinal edge of another adjacent therapy sub-array.

19. The method of claim 18, wherein aligning the focal plane of the therapeutic transducer array includes co-aligning the focal plane of the therapeutic transducer array and the imaging plane of the imaging array once the imaging array identifies the treatment site.

20. The method of claim 19, further comprising an insonation of the treatment site via the therapeutic transducer array by generating an extended focal region in an azimuthal direction and steering the extended focal region in an elevation direction, the azimuthal direction and the elevation direction with respect to direction of propagation of ultrasound beam generated by the therapeutic transducer array.

* * * * *